US011397220B2

(12) United States Patent
Ashe

(10) Patent No.: US 11,397,220 B2
(45) Date of Patent: Jul. 26, 2022

(54) DISTORTION CORRECTION FOR TRACKING AN OBJECT IN A MAGNETIC FIELD

(71) Applicant: Northern Digital Inc., Waterloo (CA)

(72) Inventor: Westley S. Ashe, Hinesburg, VT (US)

(73) Assignee: Northern Digital Inc., Waterloo (CA)

(*) Notice: Subject to any disclaimer, the term of this patent is extended or adjusted under 35 U.S.C. 154(b) by 97 days.

(21) Appl. No.: 16/838,959

(22) Filed: Apr. 2, 2020

(65) Prior Publication Data

US 2020/0319267 A1    Oct. 8, 2020

Related U.S. Application Data

(60) Provisional application No. 62/828,283, filed on Apr. 2, 2019.

(51) Int. Cl.
| | |
|---|---|
| *G01R 33/00* | (2006.01) |
| *G01B 7/30* | (2006.01) |
| *G01R 1/00* | (2006.01) |
| *H01L 21/00* | (2006.01) |

(52) U.S. Cl.
CPC .......... *G01R 33/0023* (2013.01); *G01B 7/30* (2013.01); *G01R 1/00* (2013.01); *G01R 33/0094* (2013.01); *H01L 21/00* (2013.01)

(58) Field of Classification Search
CPC ....... H01L 21/00; H01L 2221/00; G01R 1/00; G01B 1/00; G01B 2210/00
See application file for complete search history.

(56) References Cited

U.S. PATENT DOCUMENTS

| | | | |
|---|---|---|---|
| 5,347,289 A | 9/1994 | Elhardt | |
| 5,767,669 A * | 6/1998 | Hansen | F41G 3/225 324/207.12 |
| 5,847,976 A | 12/1998 | Lescourret | |
| 6,369,564 B1 | 4/2002 | Khalfin et al. | |
| 6,980,921 B2 | 12/2005 | Anderson et al. | |
| 7,532,997 B2 | 5/2009 | Li et al. | |
| 7,640,106 B1 | 12/2009 | Stokar et al. | |
| 8,040,127 B2 | 10/2011 | Jensen | |
| 9,002,437 B2 | 4/2015 | Yaroshenko et al. | |
| 9,151,822 B2 | 10/2015 | Waite et al. | |
| 10,016,148 B2 | 7/2018 | Li et al. | |
| 10,095,815 B2 | 10/2018 | Efrat et al. | |

(Continued)

OTHER PUBLICATIONS

CA Office Action in Canadian Appln. No. 3,076,356, dated May 18, 2021, 4 pages.

*Primary Examiner* — Jermele M Hollington
*Assistant Examiner* — Temilade S Rhodes-Vivour
(74) *Attorney, Agent, or Firm* — Fish & Richardson P.C.

(57) ABSTRACT

A system is configured to model a magnetic field by measuring a first value for characteristics of a magnetic field at a first position in the magnetic field. The system measures a second value characteristics of the magnetic field at a second position in the magnetic field. The system determines a distance between the first position and the second position. The system estimates a distortion component of the magnetic field at approximately the second position in the magnetic field based on each of the distance, the first value for each of the one or more characteristics, and the second value for each of the one or more characteristics. The system outputs a model of at least a region of the magnetic field.

17 Claims, 7 Drawing Sheets

(56) References Cited

U.S. PATENT DOCUMENTS

| | | |
|---|---|---|
| 2005/0107687 A1 | 5/2005 | Anderson |
| 2005/0189938 A1* | 9/2005 | Schley .................. G01D 5/252 |
| | | 324/207.15 |
| 2008/0183064 A1 | 7/2008 | Chandonnet et al. |
| 2009/0265111 A1* | 10/2009 | Helwig .................... G01V 3/12 |
| | | 702/7 |
| 2013/0169272 A1* | 7/2013 | Eichler ................. A61B 5/062 |
| | | 324/253 |
| 2016/0258782 A1 | 9/2016 | Sadjadi et al. |
| 2016/0377451 A1 | 12/2016 | Pedrotti et al. |
| 2017/0233798 A1* | 8/2017 | Neely ................. G01N 24/088 |
| | | 435/5 |
| 2017/0361726 A1* | 12/2017 | Widmer ............... B60L 53/122 |

\* cited by examiner

DISTORTION CORRECTION FOR TRACKING AN OBJECT IN A MAGNETIC FIELD

CLAIM OF PRIORITY

This application claims priority under 35 U.S.C. § 119(e) to U.S. Provisional Application Ser. No. 62/828,283, titled "DISTORTION CORRECTION FOR TRACKING AN OBJECT IN A MAGNETIC FIELD," filed on Apr. 2, 2019, the entire contents of which are hereby incorporated by reference.

TECHNICAL FIELD

This disclosure relates to tracking an object in a magnetic field, specifically determining distortions in an electromagnetic (EM) signal and correcting the distortions for tracking an object in the magnetic field.

BACKGROUND

Magnetic Tracking (MT) systems are used to aid location of instruments and anatomy in medical procedures, virtual reality (VR) settings, and augmented reality (AR) settings, among others. Such systems can determine a position of a sensor based on measured field lines of a transmitted magnetic field.

SUMMARY

An Electromagnetic Tracking (EMT) system (also referred to as a magnetic tracking system) can be used to track a device for a number of applications, such as for medical applications, AR/VR applications, and so forth. For example, in an AR/VR setting, the EMT system can be used to track the position and/or orientation of a device with respect to a head-mounted display (HMD) that is coupled to a user. The display of the HMD can show a representation of the device in an AR/VR interface at an approximate position and orientation corresponding to an actual position and orientation of the device with respect to the user. For example, in a medical setting, the magnetic tracking system can determine the position and orientation of a surgical device with respect to an operator or other reference frame. Numerous additional applications for tracking an object are known.

The magnetic tracking system is configured to determine the position and orientation of a receiver (e.g., of a tracked device) with respect to an emitter based on a magnetic signal (also referred to as a magnetic field) emitted by the emitter. Position refers to a physical location of the receiver with respect to the emitter (or vice versa), and position data can be expressed as a position vector. Orientation refers to a direction the tracked device is facing with respect to the emitter, and can be expressed as an orientation matrix. The receiver is configured to demodulate the magnetic signal received from the emitter to obtain position data representing the position of the tracked device with respect to the receiver, and to obtain orientation data representing the orientation of the receiver with respect to the emitter. In an aspect, the magnetic signal received from an emitter of the EMT system is decomposed into a signal matrix. Elements of the signal matrix each have respective magnitudes that are a function of an amplitude of the received magnetic signal and a distance between the emitter and the receiver. The calculation of position and/or orientation can be performed in a coordinate space from the perspective of the receiver (e.g., wherein the receiver represents the origin of the coordinate system). The calculation of position and/or orientation can be performed in a coordinate space from the perspective of the emitter (e.g., wherein the emitter represents the origin of the coordinate system).

In many situations, the magnetic field emitted by the emitter is distorted or at least partially distorted. In some implementations, regions of the magnetic field closer to the emitter can have relatively low distortion or be entirely undistorted. Additionally, regions further from the emitter can have relatively higher distortions. Distortions can be caused by objects in the environment of the magnetic tracking system, such as metallic objects.

The magnetic tracking system is configured to determine what distortions are present in the magnetic field emitted by the emitter so that the position and orientation of the tracked device can be accurately determined, even in the distorted regions of the magnetic field. The magnetic tracking system is configured to map the distortions of the magnetic field by comparing measurements of the magnetic field in low-distortion regions of the magnetic field to measurements of the magnetic field in higher-distortion regions of the magnetic field. Generally, the magnetic tracking system is configured to build out a model of the distortions of the magnetic field from areas near the emitter (which have low distortions) to areas further from the emitter (which may have greater distortions). Once distortions have been determined for a particular region of the magnetic field, that region becomes a trusted region and can be used as a baseline for further mapping of distorted regions (e.g., to another distorted region).

The magnetic tracking system includes an inertial measurement unit (IMU) configured to provide motion data representing motion of the tracked device. The motion data can include linear acceleration data measured by one or more accelerometers. The motion data can include angular velocity data provided by one or more gyroscopes. The IMU is coupled to the tracked device, which includes the receiver.

The motion data provided by the IMU is used by the magnetic tracking system to determine a distortion component of the magnetic field in the region of the magnetic field in which the receiver is measuring the magnetic field. The tracked device, including the receiver and the IMU, is moved from a first region of the magnetic field having low or known distortions to a second region of the magnetic field having higher and/or unknown distortions. The measured movement of the tracked device can be used to estimate the new position and orientation of the tracked device in the second region of the magnetic field relative to the emitter. The measurement of the magnetic field in the low distortion region is used to estimate an undistorted magnetic field in the second region of the magnetic field. The distortion component of the second region can be determined by finding the difference between the measured magnetic field in the second region and the estimation of the undistorted magnetic field at the second region.

The tracked device can include a first magnetic receiver and a second magnetic receiver that are coupled together on the tracked device. The first and second magnetic receivers are disposed at a predetermined distance from one another. The first and second receivers are configured to measure the magnetic field at a first region of the magnetic field and at a second region of the magnetic field, respectively. In some implementations, the first and second receivers can be configured to simultaneously measure the magnetic field at the first and second regions. Similar to the example described above, the first region is a low distortion region (e.g., a region of known distortion), and the second region is a region of greater distortion (e.g., a region of unknown distortion). The magnetic tracking system is configured to determine the distortion component of the second region by determining, based on the measurement in the first region, what the undistorted magnetic field would be at the second region. The magnetic tracking system then determines a difference between the measured magnetic field in the second region and the estimated magnetic field in the second region to determine the distortion component of the magnetic field in the second region. The second region becomes a trusted region, and can be used by the magnetic tracking system as a baseline for further mapping of the distortions (e.g., in other distorted regions of the magnetic field).

The techniques described herein include one or more of the following advantages. Absolute position reference can be obtained directly from the electromagnetic tracking system when the tracked device is located in the low distortion region of the emitted magnetic field. The EMT system can determine the position using data including only a relative position of the tracked device from the undistorted region of the magnetic field. The magnetic tracking system does not require a second tracking means (e.g., an optical means, a second tracking system, etc.) to perform distortion correction and/or obtain undistorted positions of the tracked device when the tracked device is located in the distorted region.

A sensor array of the magnetic tracking system can speed up the process of correcting the distortions of the magnetic field and generating a model of the distortions of the magnetic field, as more of the distorted region can be corrected in a given time. Redundant data available from a sensor array can assist the system for selecting which sensor(s), or a point resulting from a combination thereof (e.g., a virtual point on the tracked device), should be used to determine the position and orientation of the tracked device. The determined position and orientation can be used by the magnetic tracking system to locate the other sensor(s) in the magnetic field.

A process for distortion correction for tracking an object in a magnetic field by a magnetic tracking system includes measuring, by a magnetic sensor, a first value for each of one or more characteristics of a magnetic field at a first position in the magnetic field. The process includes measuring, by the magnetic sensor, a second value for each of the one or more characteristics of the magnetic field at a second position in the magnetic field. The process includes determining, by a computing device in communication with the magnetic sensor, a distance between the first position and the second position. The process includes estimating a distortion component of the magnetic field at approximately the second position in the magnetic field. The estimation can be based on each of the distance, the first value for each of the one or more characteristics, and the second value for each of the one or more characteristics. The process includes outputting, from the computing device based on the estimating, a model of at least a region of the magnetic field.

In an aspect, the actions include determining the distance between the first position and the second position in the magnetic field includes additional actions including measuring, by an inertial measurement unit (IMU), motion data representing movement of the magnetic sensor from the first position to the second position. The actions include determining, based on the motion data, the first value for each of one or more characteristics, and the second value for each of the one or more characteristics, the distance between the first position and the second position.

In an aspect, a first value for each of the one or more characteristics of the magnetic field is measured by a first magnetic sensor. The second value for each of the one or more characteristics of the magnetic field is measured by a second magnetic sensor that is different from the first magnetic sensor.

In an aspect, the first magnetic sensor and the second magnetic sensor are connected and separated by an offset distance. The distance between the first position and the second position in the magnetic field is approximately equal to the offset distance.

In an aspect, the first position is in a region of the magnetic field having less distortion than another region of the magnetic field including the second position. In some implementations, estimating the distortion component includes retrieving a model of the magnetic field corresponding to the second position, determining a third value of the one or more characteristics of the magnetic field corresponding to an undistorted received magnetic field at the second position according to the model, and determining a difference between the third value for each of the one or more characteristics of the magnetic field and the second value for each of the one or more characteristics that are measured at the second position. The difference represents the distortion component of the magnetic field.

In an aspect, the one or more characteristics of the magnetic field include a field strength of the magnetic field. The field strength is based on a distance of the magnetic sensor from a transmitter configured to generate the magnetic field. In some implementations, the first value for each of one or more characteristics is measured in response to determining that the magnetic sensor is in a region of the magnetic field having approximately no distortion or that the magnetic sensor is in the region of the magnetic field having a known distortion.

In an aspect, process includes expanding the region having the known distortion of the magnetic field. The first position comprises a position in the magnetic field that is inside the region having the known distortion of the magnetic field. The second position comprises a position in the magnetic field that is outside the region having the known distortion of the magnetic field.

In an aspect, the process includes determining a corrected position of the magnetic sensor in the magnetic field based on the model of at least the region of the magnetic field, generating a graphical representation of the corrected position of the magnetic sensor in the magnetic field, and causing display of the graphical representation in a user interface.

In an aspect, the magnetic tracking system includes a source device configured to generate a magnetic field. The magnetic tracking system includes a tracked device that includes a magnetic sensor configured to measure the magnetic field and generate magnetic data representing the magnetic field and an inertial measurement unit (IMU) configured to generate motion data based on a motion of the IMU. The IMU is coupled to the magnetic sensor. The magnetic tracking system includes a computing device that includes at least one processor. The computing device is configured to perform the following operations. The operations include receiving, from the magnetic sensor, first magnetic data representing a first position of the magnetic sensor. The operations include receiving, from the magnetic sensor, second magnetic data representing a second position of the magnetic sensor. The second position is in a relatively more distorted region of the magnetic field than the first position. The operations include determining a distance between the first position and the second position based on motion data received from the IMU representing motion of the magnetic sensor from the first position to the second position. The operations include determining, based on the distance, the first magnetic data, and the second magnetic data, a distortion component of the magnetic field. The operations include outputting a model of the magnetic field based on the distortion component.

In an aspect, the magnetic tracking system can include a transmitter is configured to generate the magnetic field. The transmitter is configured to generate a magnetic field including a plurality of axes using a plurality of transmitter axes. The magnetic sensor is configured to measure the magnetic field by measuring each of the transmitted axes of the magnetic field. In some implementations the motion data comprises linear acceleration data and angular acceleration data. The IMU comprises one or more accelerometers and one or more gyroscopes.

In an aspect, estimating the distortion component by the magnetic tracking system includes retrieving a model of the magnetic field corresponding to the second position, determining a value of the magnetic field corresponding to an undistorted received magnetic field at the second position according to the model, and determining a difference between the value of the magnetic field and a value of the second magnetic data that is measured at the second position. The difference represents the distortion component of the magnetic field. In some implementations, the operations further include determining a corrected position of the magnetic sensor in the magnetic field based on the model the magnetic field, generating a graphical representation of the corrected position of the magnetic sensor in the magnetic field, and causing display of the graphical representation in a user interface.

In an aspect, the magnetic tracking system includes a source device configured to generate a magnetic field. The magnetic tracking system includes a tracked device including a first magnetic sensor configured to measure the magnetic field and generate magnetic data representing the magnetic field at a first position relative to the source device. The tracked device includes a second magnetic sensor coupled to the first magnetic sensor at a particular distance and configured to measure the magnetic field and generate magnetic data representing the magnetic field at a second position relative to the source device and at the particular distance from the first position. The magnetic tracking system includes a computing device including at least one processor. The computing device is configured to perform operations including receiving, from the first magnetic sensor, first magnetic data representing the magnetic field at the first position, receiving, from the second magnetic sensor, second magnetic data representing the magnetic field at a second position, the second position being in a relatively more distorted region of the magnetic field than the first position, determining, based on the particular distance, the first magnetic data, and the second magnetic data, a distortion component the magnetic field, and outputting a model of the magnetic field based on the distortion component.

In some implementations, estimating the distortion component includes retrieving a model of the magnetic field corresponding to the second position, determining a value of the magnetic field corresponding to an undistorted received magnetic field at the second position according to the model, and determining a difference between the value of the magnetic field and a value of the second magnetic data that is measured at the second position, the difference representing the distortion component of the magnetic field.

In an aspect, the magnetic tracking system is configured to include non-transitory computer readable medium storing instructions that are executable by one or more processors configured to perform operations including obtaining, from a magnetic sensor, a first value for each of one or more characteristics of a magnetic field at a first position in the magnetic field. The operations include obtaining, from the magnetic sensor, a second value for each of the one or more characteristics of the magnetic field at a second position in the magnetic field. The operations include determining, a distance between the first position and the second position. The operations include estimating, based on each of the distance, the first value for each of the one or more characteristics, and the second value for each of the one or more characteristics, a distortion component of the magnetic field at approximately the second position in the magnetic field. The operations include outputting, based on the estimating, a model of at least a region of the magnetic field.

The details of one or more embodiments of the subject matter described herein are set forth in the accompanying drawings and the description below. Other features, objects, and advantages of the subject matter will be apparent from the description and drawings, and from the claims.

DESCRIPTION OF DRAWINGS

Like reference symbols in the various drawings indicate like elements.

DETAILED DESCRIPTION

An Electromagnetic Tracking (EMT) system (also called a magnetic tracking system) can be used in medical settings, virtual reality (VR) settings, augmented reality (AR) settings, etc., to track a device. For example, in a surgical setting, the EMT system can be used to track medical equipment, robotic arms, etc., thereby allowing the three-dimensional position (e.g., location) and the orientation of the device to be known to a medical professional (e.g., a surgeon) during a medical procedure.

In many situations, a magnetic field emitted by an emitter (of an EMT system) is distorted or at least partially distorted. In some implementations, regions of the magnetic field closer to the emitter can have relatively low distortion or be entirely undistorted. Additionally, regions further from the emitter can have relatively higher amounts of distortion. Such distortions can be caused by objects in the environment of the magnetic tracking system, such as metallic objects.

The magnetic tracking system is configured to determine what distortions are present in the magnetic field emitted by the emitter so that the position and orientation of the tracked device can be accurately determined, even in the distorted regions of the magnetic field. The magnetic tracking system is configured to map the distortions of the magnetic field by comparing measurements of the magnetic field in low-distortion regions (e.g., regions of known distortions, undistorted regions, etc.) of the magnetic field to measurements of the magnetic field in higher-distortion regions (e.g., regions of unknown distortions, etc.) of the magnetic field. Generally, the magnetic tracking system is configured to produce a model of the distortions of the magnetic field from areas near the emitter (typically having low distortions) to areas further from the emitter (which may have greater distortions). Once distortions have been determined for a particular region of the magnetic field, that region can be considered a trusted region and can be used as a baseline for further mapping of distorted regions (e.g., to another distorted region).

Figure 1A:
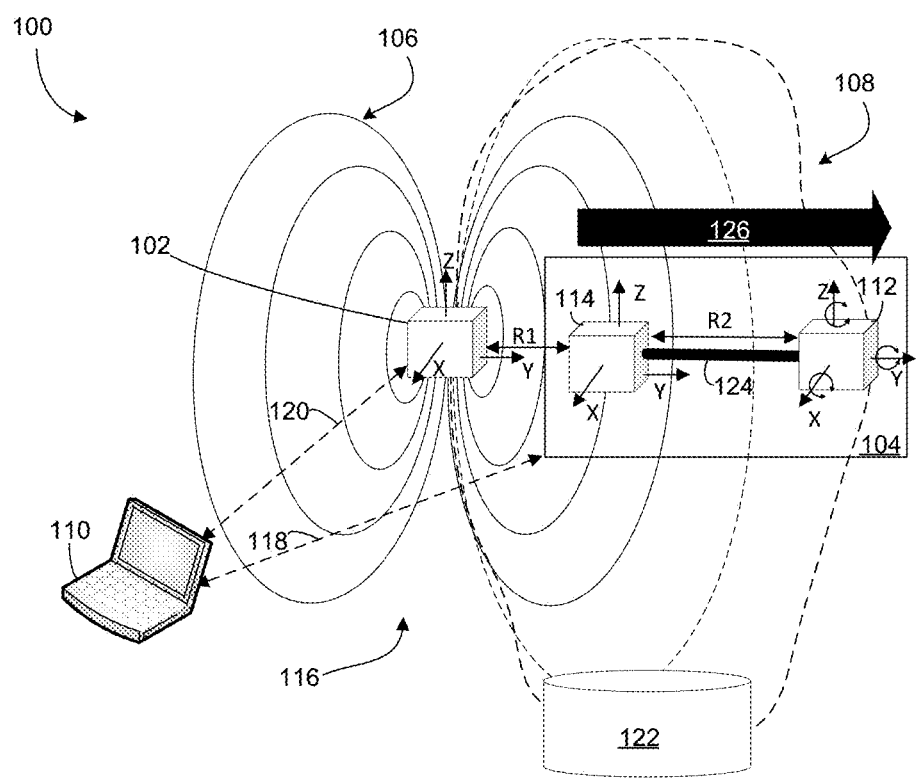
FIG. 1A shows an example of a magnetic tracking system including an Inertial Measurement Unit (IMU).

FIG. 1A shows an exemplary embodiment of a magnetic tracking system 100, which can be used for determining a position of a tracked device 104 (e.g., a surgical scalpel?) in a magnetic field 116 relative to a tracking device 102 of the magnetic field. In general, the tracking device 102 includes an emitter (also referred to as a source) that is configured to generate the magnetic field 116 (e.g., a magnetic signal), such as by one or more field-emitting coils.

The tracked device 104 of the system 100 includes a magnetic field receiver 114 (also called a magnetic sensor) that is configured to measure characteristics of the magnetic field 116, for example, by employing one or more field-measuring coils. The tracked device 104 also includes an inertial measurement unit (IMU) 112 configured to generate motion data based on movement of the tracked device 104. The receiver 114 is configured to measure the magnetic field 116 and determine a distance R1 that the tracked device 104 is displaced from the tracking device 102. For example, knowing the strength of the magnetic field at the tracking device 102 and the field strength at the receiver 114, the distance R1 can be calculated. In FIG. 1A, the distance R1 is along the y-axis of the coordinate system, but the tracked device 104 can be positioned anywhere in the magnetic field 116 relative to the tracking device 102 and the distance can be represented with other coordinates (e.g., x-axis coordinates, z-axis coordinates, coordinate combinations, etc.).

The receiver 114 is configured to measure position data in the magnetic field 116 with respect to the emitter of the tracking device 102. The position of the tracked device 104 represents a physical location of the receiver 114 with respect to the emitter of the tracking device 102 (or vice versa). In some implementations, position data can be expressed as a position vector of position coordinates (e.g., x, y, z coordinates). Various perspectives can be employed to define a coordinate system (e.g., for quantifying distances, etc.); for example, a system in which the tracking 102, the tracked device 104, etc. can be placed at the origin of the coordinate system. In this example, the receiver 114 uses a Cartesian coordinate system (with x, y, and z coordinates) to represent space; however, other types of coordinate systems (e.g., cylindrical, spherical, etc.) may be utilized.

The receiver 114 is mechanically coupled to the IMU 112. For example, the receiver can be coupled to the IMU 112 by a member 124 (e.g., a bar or other type of structure and the member 124 can be a rigid or semi-rigid material. The length of the rigid member 124 is generally known, so that the distance R2 between the receiver 114 and the IMU 112 is known by the magnetic tracking system 100. Being known, the distance R2 can be used by the magnetic tracking system 100 to determine the position of the receiver 114 in the magnetic field 116. For example, when the tracked device 104 is moved, rotated, etc. in the magnetic field 116 the IMU 112 generates inertial data (e.g., motion data). The distance R2 is used to determine a trajectory of the receiver 112 moving in the magnetic field 116, such as illustrated by arrow 126. The dimensions of the member 124 (which are known by the magnetic tracking system 100) are used by the tracking system to determine the position of the receiver 114 with respect to the IMU 112. In the example of FIG. 1A, the IMU 112 is displaced R2 along a y-axis from the receiver 114. For example, if the IMU 112 is rotated about the x-axis, the magnetic tracking system 100 can determine that the trajectory of the receiver is an arc with radius R2 through the magnetic field 116. The IMU 112 is configured to measure the motion (e.g., linear and angular accelerations) of the tracked device 104 through the coordinate system (e.g., along the three coordinate axes). Potential rotations and/or movements about x, y, and z axes are shown in FIG. 1A represented by graphical symbols associated with each individual axis.

The orientation of the tracked device 104 refers to a direction the tracked device is facing with respect to the tracking device 102, and can be expressed similarly by using a coordinate system and represented, for example, as a vector of orientation coordinates (e.g., azimuth ($\psi$), altitude ($\theta$), and roll ($\varphi$) angles). While orientation can be represented as coordinates in the perspective of the tracked device 102 where the tracked device 104 is the origin, orientation can alternatively be represented as a coordinates in the perspective of the tracking device 102, in which the emitter is the origin. In this way, the tracked device 104 may act as a six degree of freedom (6DoF) sensor that is configured to allow for measurement of position and orientation information related to a forward/back position, up/down position, left/right position, azimuth, altitude, and roll.

The motion data represents motion of the tracked device 104 relative to a fixed device of an environment of the system 100 (e.g., global acceleration values such as gravity are corrected by normalizing the motion data). Various types of motion (e.g., linear and/or angular velocity, linear and/or angular acceleration, etc.) may be determined by employing one or more measurement techniques. For example, motion data can include linear acceleration data measured by one or more accelerometers, angular velocity data provided by one or more gyroscopes, etc.

The tracking device 102 includes a transceiver (not shown) that generally includes a transmitter and a receiver. In one example the transceiver is connected to an antenna and is configured to receive motion data from the IMU 112 of the tracked device 104 by a communication channel (e.g., over a wireless communication channel). For example, the tracking device 102 is configured to provide the measurements (e.g., position and orientation measurements) of the tracked device 104 to a computing device 110, e.g., over a channel 120. The computing device 110 determines information related to the tracked device 104 (e.g., position information, orientation information, both, etc.) based on the measurements. In some implementations, the tracked device 104 is configured to send the position and orientation data directly to the computing device 110, such as over a channel 118. The motion data can be transmitted from the tracked device 104 to the tracking device 104 by communication protocols such as Bluetooth, WiFi, ZigBee, etc.

In some aspects, the tracking device 102 is coupled to a head-mounted display (HMD) that can be worn by a user and provide a graphical user interface to the user. The tracking device 102 can be coupled to (or otherwise a part of) a computing device 110 configured to perform the calculations for determining the position and the orientation of the tracked device 102 for the system 100. The tracked device 104 can be one or more of a controller, a surgical tool, etc. that is represented by the HMD. For example, a surgeon (or other user) can view a representation of a scalpel which accounts for the position and orientation of this surgical tool with respect to the relative location of the surgeon.

The computing device 110 comprises one or more processors and is configured to receive the position data, the orientation data, and the motion data that are measured and/or received by the tracking device 104. The tracked device 104 measures the magnetic signal 116 emitted by the tracking device 104 and converts the magnetic signal into position data and orientation data that can be processed by the computing device 110. In some aspects, the tracking device 102 is a part of the computing device 110. In situations where the tracking device 102 is a part of the computing device 110, the description can refer to the computing device and the tracking device interchangeably as disambiguating the position data and the orientation data.

The computing device 110 is configured to determine one or both of the position and the orientation of the tracked device 104 based on the received magnetic signal representative of the measured characteristics of the magnetic field 116. In some examples, the computing device 110 may determine the position and/or orientation of the tracked device 104 relative to the position and/or orientation of the tracking device 102.

In some implementations, the tracked device 104 is configured to demodulate the magnetic signal 116 received from the emitter to obtain position data representing the position of the tracked device 104 with respect to the tracking device 102, and to obtain orientation data representing the orientation of the tracked device 104 with respect to the tracking device 102. In some implementations, the magnetic signal 116 is associated with a particular frequency that the tracked device 104 can associate with the tracking device 102 to distinguish the tracking device from one or more other devices that may be emitting (electro) magnetic signals at other frequencies.

The tracking device 102 can tag the position data, orientation data, and motion data received from the tracked device 104 with a device identifier. The computing device 110 can determine which device the position data, orientation data, and motion data are associated with based on the identifier, and use this information for one or more applications. For example, the computing device may generate a user interface in which the tracked device 104 is being represented along with other tracked devices. For example, the position and orientation of the tracked device 104 are reported, etc.

The magnetic field 116 generally includes a low-distortion region 106. The low-distortion region 106 can also be referred to as a region of less distortion (e.g., relative to another region of the magnetic field 116) or an undistorted region of the magnetic field. The lower-distortion region 106 is generally nearer to the emitter relative to other portions of the magnetic field 116. The lower-distortion region 106 generally is similar to an ideal magnetic field and can provide a baseline for determining the distortions of the magnetic field 116 in other regions of the magnetic field. Generally, the magnetic field 116 is stronger nearer to the emitter (e.g., of the tracking device 102) and weaker further from the tracking device. In some implementations, the magnetic field 116 intensity is inversely proportional as a function of the distance R1 from the emitter, such as a cubic decay (e.g., $1/R1^3$).

In many cases, the magnetic field 116 emitted by the emitter of the magnetic tracking system 100 is distorted by one or more objects 122 present in the environment of the magnetic tracking system 100. While the object 122 may be a portion of the magnetic tracking system 100, generally the object is not a portion of the magnetic tracking system. For example, the object 122 can include furniture, such a metal operating table, surgical instruments, suspended ceilings, filing cabinets, electronics, or any other object, generally at least partially metallic, that can cause distortions to the magnetic field 116.

When the object 122 causes distortions in magnetic field 116 of the magnetic tracking system 100, the magnetic field includes a distorted region 108 (denoted by dotted field lines in FIG. 1A). The distortions can include deviations from an ideal dipole filed shape, as is known in the art. Generally, the distortion effect is proportional to the distance R1 of the tracked device 104 from the emitter. For example, the distortion can be an exponential function (e.g., $R1^6$) of the distance from the emitter. Therefore, the magnitude of the distortions of the magnetic field 116 are greater at further distances (greater values of R1) from the emitter than at nearer distances (smaller values of R1) from the emitter of the tracking device 102.

To determine the position of the tracked device 104 in the magnetic field 116, the magnetic tracking system 100 is configured to receive a measurement of the magnetic field from the receiver 114 of the tracked device 104 in the lower-distortion region 106 of the magnetic field. The tracked device 104 is moved to the higher-distortion region 108 of the magnetic field 116 as shown by arrow 126. The receiver 114 measures the magnetic field 116 in the higher-distortion region 108. In addition, a trajectory of the tracked device 104 is measured by the IMU 112 as the tracked device 104 moves from the lower-distortion region 106 to the higher-distortion region 108. In some implementations, the motion data and each of the magnetic field 116 measurement in the higher-distortion region 108 (high-distortion measurement or second magnetic field measurement) and the lower-distortion region 106 (low-distortion measurement or first magnetic field measurement) that are each captured by the tracked device 104 are sent to the computing device 110 for computation of the position of the tracked device 104. As stated above, the computation can be performed at any of the tracked device 104, tracking device 102, or a remote computing device 110, which is shown in FIG. 1A.

The computing device 110 determines the trajectory of the tracked device 104 which includes an estimate of the relative position of the tracked device 104 with respect to an original position of the tracked device 104 (e.g., when the tracked device 104 measures the magnetic field 116 in the lower-distortion region 106). The computing device 110 (or the IMU 112) is configured to double integrate each three-axis accelerometer signal (respectively representing x, y, and z coordinates) after compensating for gravitational acceleration. A single integration is performed on the outputs of the gyroscope which provide azimuth, elevation, and roll angles.

The computed trajectory is correlated with the lower-distortion measurement to form a reference frame (e.g., perspective) for the tracked device 104. Errors in the linear acceleration (e.g., due to gravitational effects) obey the function of $$\text{Position Error} = 0.5(Ae) * T^2 \quad (1)$$

where Ae is the error in acceleration measurements and where T is the elapsed time between measurements.

The computing device 110 thus estimates, based on the motion data received and the measurement of the magnetic field 116 in the lower-distortion region 106, an approximate position of the tracked device 104 in the magnetic field 116 after the tracked device is moved. The updated position is a position relative to the tracking device. The position of the tracked device 104 is known with high confidence when the tracked device is in the lower-distortion region 106. Because of this, the computing device 110 determines the relative position of the tracked device 104 from the initial position of the tracked device when the magnetic field 116 is measured in the lower-distortion region 106. The error introduced as shown by Eq. 1.

The computing device 110 estimates what the undistorted magnetic field should be at the estimated position (e.g., in accordance with an ideal magnetic dipole). The measured magnetic field 116 at the updated position is compared to the ideal baseline. When the tracked device 104 is in a higher-distortion region 108, the difference is larger than when the tracked device is in a lower-distortion region 106. The difference between the measured magnetic field 116 and the estimated magnetic field 116 is treated as the distortion component of the magnetic field and mapped to the updated location of the tracked device 104 to generate a model of the distortions in the magnetic field.

The magnetic tracking system 100 uses the statistical error probability of the accelerometer to determine how far a trusted zone of the magnetic field 116 can be expanded before another high-confidence, low distortion measurement of the magnetic field 116 is needed from the tracked device 104. Here, the trusted zone refers to a region of the magnetic field 116 in which approximate distortion levels are known and for which the magnetic tracking system 100 can compensate for distortion in the measurement of the magnetic field 116 to report an accurate position of the tracked device 104. In other words, the trusted zone initially includes the lower-distortion region 106 (typically near the tracking device). As the tracked device 104 determines a distortion component of the magnetic field 116 for various locations in the higher-distortion region 108, those portions become regions of known distortion. Those various locations can be used as a basis for further approximation of the distortions of the magnetic field 116 deeper into the higher-distortion region 108, further away from the lower-distortion region 106 (e.g., further along arrow 126). In this way, the distortions of the magnetic field 116 are modeled incrementally, which reduces errors in the position approximation of the tracked device 104 that can be introduced from the motion data. In other words, smaller distances in the movement of the tracked device 104 (e.g., along arrow 126) between estimates of the distortion component of the magnetic field 116 generally have relatively smaller errors in the distortion estimation (and thus the corrected position estimate). Larger distances between estimates of the distortion component in the higher-distortion region 108 can result in relatively larger errors in the distortion approximation.

The trusted region expansion that is performed by the magnetic tracking system 100 can be mathematically described. Generally, the lower-distortion region 106 does not contain magnetic distorters. Rather distorters (such as object 122) tend to exist in the space surrounding the lower-distortion region 106 where the tracked device 104 is being tracked. The magnetic field from a single distorter 122 can be modeled as $M = (T*K)/R_d^3$ where M is the magnetic moment of the distorter, T is the magnetic moment of the emitter, K is a proportionality constant dependent on the particular distorter 122, and $R_d$ is the range of said distorter from the emitter. The magnetic field at the magnetic field receiver 114 due to said distorter is proportional to $M/R_{sd}^3$, where $R_{sd}$ is the range from the tracked device 104 to the distorter 122. For distorters outside of the tracking volume (e.g., where the tracked device 104 is being tracked), the ratio of transmitted field to distorter field can be described as $\text{Ratio} = T/R_t^3 / (T*K/R_d^3) * (M/R_{sd}^3)$. The magnetic field 116 decays in proportion to $1/R_t^3$ and the distorter field at the tracked device 104 decays in proportion to approximately the cube of the total distance from the emitter to distorter 122 plus distorter to tracked device 104. Generally, magnetic field receiver(s) (e.g., receiver 114) are significantly less affected by distorter(s) 122 outside of the tracking volume when the magnetic field receiver(s) are closer to the emitter.

One example model for a distorter 122 is a conductive loop. The vector components of the magnetic field at the magnetic field receiver due to this distorter can be expressed as:

$$B_i^{dist}(\vec{r}_{ds}) = I\vec{a} \cdot \vec{B}^{dip,i}(\vec{r}_{ds})$$

where $r_{ds}$ is the distance between the distorter and magnetic field receiver, I is the current in the loop, m is the vector area of the loop, and $B^{dip,i}$ is the field of a unit dipole aligned along the i-axis. The emitter provides the energy to drive the current which can be expressed:

$$I = k\vec{B}^{xmtr}(\vec{r}_{xd}) \cdot \vec{a}$$

where k is a constant dependent on the emitter frequency and material properties of the conductive loop, $B^{xmtr}$ is the field of the emitter, and $r_{xd}$ is the position vector from the emitter to the distorter.

An expression for the distorter's field is:

$$B_i^{dist}(\vec{r}_{ds}, \vec{r}_{xd}) = k[\vec{B}^{xmtr}(\vec{r}_{xd}) \cdot \vec{a}][\vec{a} \cdot \vec{B}^{dip,i}(\vec{r}_{ds})]$$

The magnetic field of the emitter is approximated as that of a dipole, which drops off as $1/r^3$. Therefore, the magnitude of the distorter's field relates to its proximity to both the emitter and receiver can be expressed as:

$$|B^{dist}(\vec{r}_{ds}, \vec{r}_{xd})| \propto \frac{1}{(r_{ds} r_{xd})^3}$$

The magnitude of the emitter's field at the receiver is proportional to the cube of the distance between those two:

$$|B^{xmtr}(\vec{r}_{xs})| \propto \frac{1}{r_{xs}^3}$$

Therefore, as long as the product of the distances of distorter-to-emitter and distorter-to-magnetic field receiver 114 is larger than the distance of receiver-to-emitter, then the field of the emitter at the magnetic field receiver will dominate over the distorter 122.

The initial position of the tracked device 104 (e.g., in the trusted region or in the lower-distortion region 106) can be determined in several ways. The initial position can be a location within a threshold radius of the tracked device 104. The initial position can be designated by a user. For example, a user can move the tracked device 104 to a location within the lower-distortion region 106. The magnetic tracking system 100 may indicate to the user (e.g., by a user interface) the position of the tracked device 104 based on measurements of the magnetic field 116 with no distortion model. When the tracked device 104 is in the lower-distortion region 106, the reported position of the tracked device 104 (e.g., relative to the tracking device 102) is near to the actual location of the tracked device, as seen by the user. The magnetic tracking system 100 can use various other means for verifying the initial position of the tracked device 104, such as using a contact (e.g., a metal contact such as a charging station for the tracked device 104), a touch sensor, a control manipulated by a user, etc. to verify that the initial position of the tracked device 104 is in a lower-distortion region 106 of the magnetic field 116. For example, the user can press a button when the position of the tracked device 104 represented by the magnetic tracking system 100 accurately corresponds to the actual position of the tracked device 104.

In some aspects, an error estimation module (not shown) of the computing device 110 is configured to determine an error of the relative position of the tracked device 104 from the motion data of the IMU 112. The computing device 110 can determine an approximate location of the tracked device 104 to a resolution according to the error value. The computing device 110 can determine the position error based on parameters including elapsed time, bias error, linearity, sensor resolution, and so forth. If the error value is below a threshold, the estimated relative position value of the tracked device 104 is added to the initial position having been verified as described above to result in an absolute position of the tracked device relative to the tracking device and emitter. The computing device 110 determines the idea magnetic field at the estimated absolute position of the tracked device 104 and subtracts it from the measured magnetic field 116 at that location.

Figure 1B:
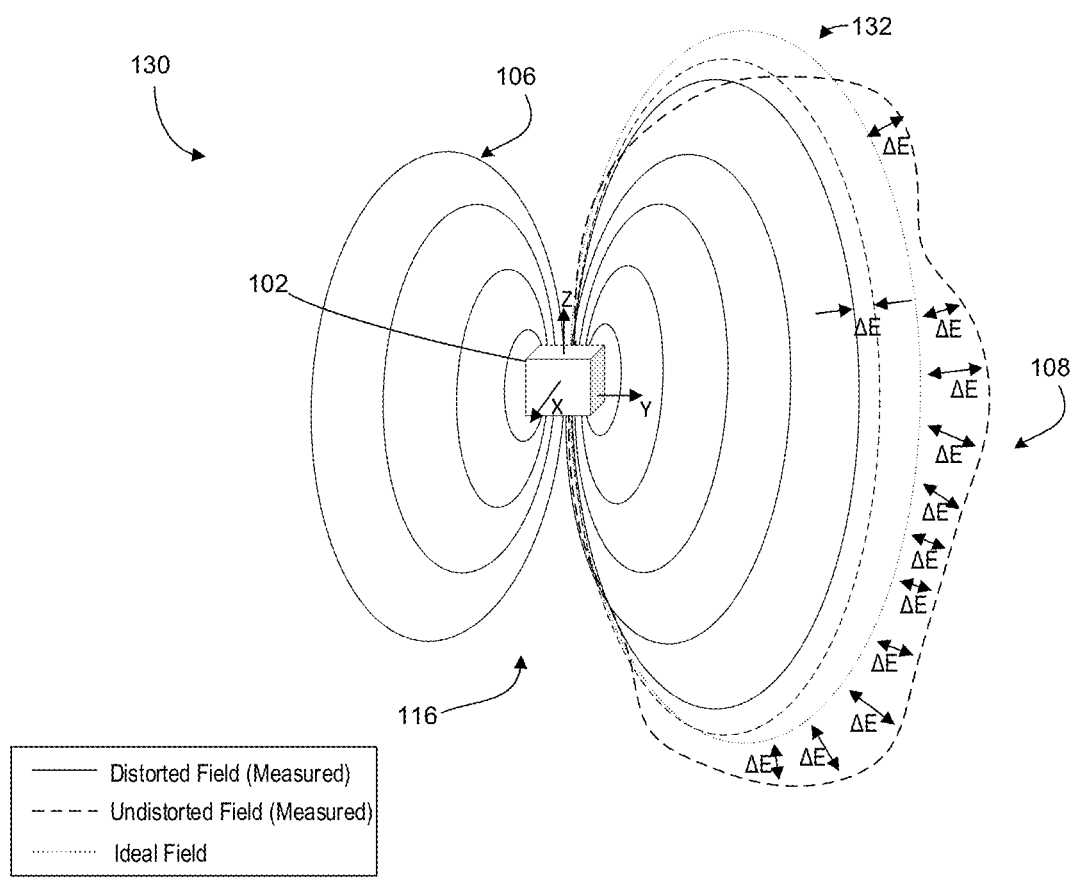
FIG. 1B shows an example representation of an error map generated based on measurements form the magnetic tracking system of FIG. 1A.

The computing device 110 generates an error map (also referred to as a distortion error field, error field map, or a distortion field) as a model for further position determinations. Turning to FIG. 1B, an example of an error map is shown. The difference ΔE between the measured field 116 and the ideal field 132 is determined mapped in a coordinate space. Although ΔE appears one-dimensional in FIG. 1B, the difference ΔE is determined in all directions. For example, the error field can be defined in the perspective of the tracking device 102. The error map includes x, y, and z vector components of the distortion at each location in which a measurement of the magnetic field 116 is acquired by the receiver 114. The computing device combines several error fields (e.g., one from each measurement of the magnetic field 116) into the error map.

The error map is used to adjust further measurements of the magnetic field 116. If the error map at a particular location reduces the difference between the measured magnetic field 116 at that location by the tracked device 104 and an ideal magnetic field estimated for that location below a threshold, the computing device 110 defines that location as a distortion-corrected location and adds that location (e.g., a region near that location in accordance with position error estimations described above) to the trusted region of the magnetic field 116. The trusted region magnetic field 116 can then be used as a basis for further distortion mapping of the higher-distortion region 108. The trusted region includes the same position confidence as an undistorted region. In some implementations, some error value can still be present in the position determination in an undistorted region due to hardware constraints. This potential error can be handled by calibration of the hardware (e.g., a one-time calibration) or handled in a similar manner.

The error mapping process can be performed in one or more of several ways. For example, the error mapping can include optimizing of the model of external dipole sources. The error mapping can include optimizing a Taylor expansion of the fields. In another example, the error mapping includes a field map where a multi-dimensional lookup table is queried for position value based on a plurality of measured fields. In yet another example, the error mapping includes a correction map in which the magnetic field 116 measurements of the receiver 114 of the tracked device 104 are corrected directly by the computing device 110 by re-mapping locations without regard to the measured fields, as described in U.S. application Ser. No. 16/838,878, titled CORRECTING DISTORTIONS, filed Apr. 2, 2020, issued as U.S. Pat. No. 11,187,823, the contents of which are hereby incorporated by reference in entirety.

Figure 2:
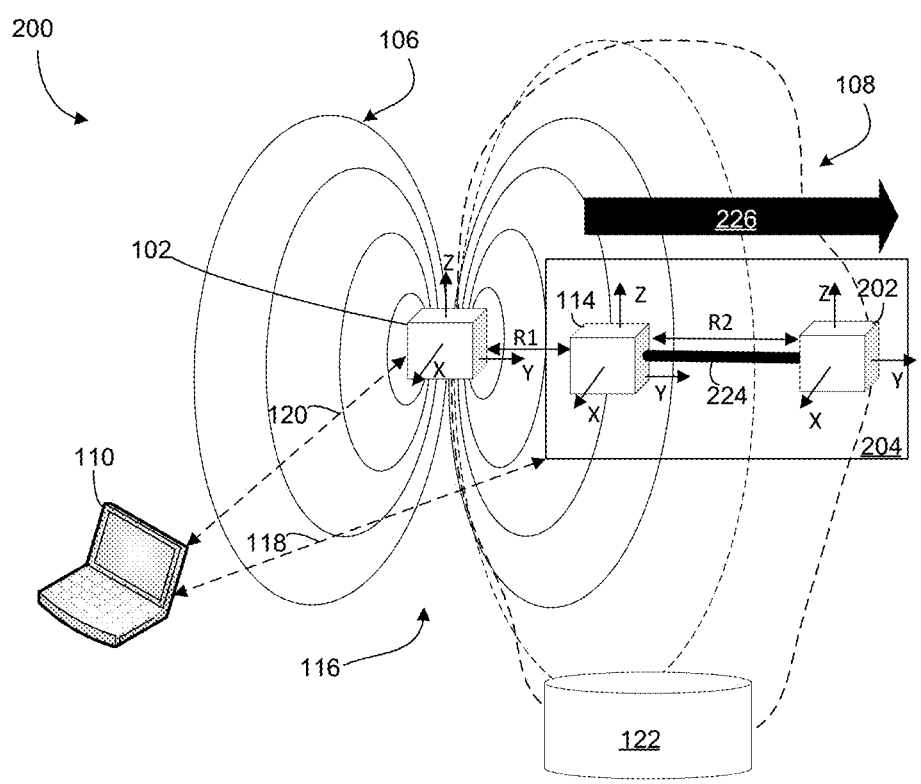
FIG. 2 shows an example of a magnetic tracking system including a first magnetic field receiver and a second magnetic field receiver.

Turning to FIG. 2, a magnetic tracking system 200 is shown. The magnetic tracking system 200 is similar to the magnetic tracking system 100 of FIG. 1A, except that tracked device 204 does not have an IMU. Rather, the tracked device 204 includes a first receiver (which is substantially similar to receiver 114 of FIG. 1A) and a second receiver 202 that measures the magnetic field 116 along with the first receiver 114 for the tracked device 204. Generally, the second receiver 202 is substantially similar to the receiver 114, and is configured to measure the magnetic field 116 at a second position along with the first receiver 114 being configured to measure the magnetic field 116 at a first position. The second receiver 202 is configured to measure the magnetic field 116 at a distance R2 from the first receiver.

The first receiver 114 and the second receiver 202 are displaced from one another at a distance R2. A rigid or semi-rigid member 224 couples the first receiver 114 and the second receiver 202 together at distance R2. While it is not required that R2 be a fixed distance (e.g., member 224 can be of adjustable length or size), the distance R2 is known by the computing device 110. For example, the member 224 can include an extendable rod that can adjust to different lengths. Generally, the member 224 is of fixed size. In some implementations, the member 224 does not include a rod (as shown in FIG. 2), but can be any coupling mechanism that couples the first receiver 114 to the second receiver 204 at fixed or variable distance R2. For example, the distance R2 can be 2, 4, 6, 8, 10, etc. inches. While any practical distance R2 can be used, the distance R2 is generally about 6-8 inches.

The computing device 110 is configured to determine the distortion component of the magnetic field 116. The tracked device 204 is configured to measure the magnetic field 116 at a first location in the trusted zone of the magnetic field 116, which can initially include the lower-distortion region 106. The magnetic tracking system 200 can determine the lower-distortion region 106 in a manner similar to the magnetic tracking system 100 of FIG. 1A.

The magnetic tracking system 200 obtains, by the first receiver 114, a first measurement of the magnetic field 116 in the lower-distortion region 106 (or in the trusted zone in subsequent iterations). The first measurement of the magnetic field 116 is obtained in a manner similar to that described in relation to FIG. 1A. The second receiver 202 is configured to obtain a second measurement of the magnetic field 116 by the distance R2. Generally, the location of the receiver 202 when the second measurement is taken is in the higher-distortion region 108.

The computing device 110, based on the first measurement of the magnetic field 116 obtained by the first receiver 114, determines an ideal magnetic field (also called an undistorted magnetic field) value for the position of the first receiver. The computing device 110 determines what the ideal magnetic field should be at the position of receiver 202 based on the known distance R2. The position of the second receiver 202 is determined based on the orientation of the first receiver 114.

The roles of the first and second receivers 114, 202 can alternate based on the position of the tracked device 204. For example, if the second receiver 202 is within the lower-distortion region 106 (or the trusted region), the second measurement of the magnetic field 116 can be used as a basis for estimating the distortion of the magnetic field at the position of the first receiver 114. For example, in a subsequent iteration, the roles of the receivers 114, 202 can revert back to the original configuration if the first receiver 114 is determined to be within the trusted zone and the second receiver 202 is not within the trusted zone.

To obtain a greater increase in trusted region size, the first and second receivers are generally radially aligned with the tracking device 102 when measurements of the magnetic field 116 are obtained. This is because the magnetic field 116 distortion tends to be greater as the value of R1 increases. However, this configuration is not necessary for functionality of the magnetic tracking system 200. The second receiver 202 can be distance by R2 in any direction from the first receiver 114, and can be in a lower-distortion region 106 or a higher-distortion region 108. The trusted region is expanded when the first (or second) receiver is in the trusted region and the other receiver is outside of the trusted region. If both the first and second receivers 114, 202 are outside of the trusted region, the trusted region is generally not expanded. If both the first and second receivers 114, 202 are inside the trusted region, the error map that is generated (e.g., as described in relation to FIG. 1B) can be improved using updated measurements.

Once the two measurements of the magnetic field 116 are obtained, the computing device 110 can determine a distortion component of the magnetic field at either the first or second receiver in a manner similar to that described in relation to FIG. 1A. For example, the ideal field, measured by the first receiver 114, is projected to the determined position of the second receiver 202, and determines the difference between the actual measured magnetic field 116 value and the ideal magnetic field at the position of the second receiver 202. The error map is built in a manner similar to that which is described in relation to FIG. 1A.

Once the distortion component of the magnetic field 116 has been mapped for the location of one or both of the receivers 114, 202, the tracked device 204 can be moved and the process repeated to expand the trusted region. For example, the tracked device 204 can be moved away from the tracking device 102 as shown by arrow 226. If one of the two receivers 114, 202 remains in the trusted region (even the expanded trusted region), the trusted region can again be expanded on the next iteration. For example, if the distance R2 is 8 inches, the tracked device 204 can be moved up to 8 inches out of the trusted zone, and the process repeated to expand the trusted zone by that amount.

Measurements of the magnetic field 116 by receivers 114, 202 need not be simultaneous, but are generally close in time to one another. If the tracked device 204 is stationary, a longer period of time can pass between measurements by the receivers 114, 202. If the magnetic field 116 is static, any amount of time may pass between measurements by receivers 114, 202 when the tracked device 204 is stationary.

Other embodiments of the magnetic tracking systems 100, 200 are possible. For example, tracked device 104, 204 can be moved back and forth in region near the boundary of the trusted zone until the position of the tracked device 104, 204 that is determined by the computing device 110 does not change or changes less than a threshold amount on subsequent iterations. Slight differences in position estimation can occur due to the errors in trajectory calculation or due to errors in other estimations (e.g., of the ideal magnetic field at for a position of the tracked device 104, 204). By repeating the process in a region, the confidence of the error field map, and thus the model of the distortions, can be increased.

To determine when prior measurements, which may be less reliable or unreliable should be updated, the following processes can be used. Magnetic tracking systems typically create a matrix of mutual inductances between the numerous sensor and emitter coils. The emitter coil arrangement is commonly referred to as an emitter constellation. The constellation is characterized during the manufacturing process by analysis or mapping such that the field vector from each coil is known as a function of position relative to that coil. For a perfect, error free sensor position relative to the emitter constellation, each of the mutual inductance values in the matrix are exactly predictable from the reported sensor position, though generally this is not the case. Depending on the type of constellation used in a particular system, the receiver 114 position is commonly computed by using a least squares algorithm, such as Levenberg-Marquardt, or from the dipole algorithm. In either case, the measured mutual inductance matrix values generally do not correspond exactly to the theoretical values at the best prediction of sensor position. This error is generally referred to as a residual error and can be used as a confidence indicator for the reliability of the position output. A higher residual error is indicative of matrix values which do not fit the model and are thus likely distorted. Thus the residual from these algorithms can be an indicator of position error in the solution output. In the case of the magnetic tracking system 100, sensor position values which possess a relatively lower residual can be selected as reference values for use in correcting those with relatively higher residuals.

Additional receivers can be added to the tracked device 104, 202 to increase the confidence of the distortion estimation for a particular measurement iteration. For example, the tracked device 104 can include two receivers. For example, the tracked device 104, 202 can include three, four, or more receivers at known distance s from one another. The processes described above for the tracked device 104 and the tracked device 204 can be combined, and the trajectory reported by the IMU 112 and magnetic field 116 measurements from multiple receivers can be used to estimate the distortion of the magnetic field.

In an aspect, the lower-distortion region 106 can be a region that is displaced from the emitter and not include a region near the emitter. For example, if an object 122 is near the emitter, there may be a lower-distortion region 106 at a further distance from the emitter than a higher-distortion region 108 nearer to the emitter of the tracking device 102.

The magnetic tracking system 100, 200 can be used to detect that distortion is present in a region and report that the distortion is at a particular position and an approximation of the distortion at that position relative to the tracking device 102. For example, a user interface of the magnetic tracking system 100, 200 can inform the user that distortion has been detected with an indicator.

In an aspect, the computing device 110 can at least partially use electromagnetic pose data to determine the position of the tracked device 104, 204 in the trusted region and the higher-distortion region 108 for correcting the distortion. For example, a Kalman pose estimation can be used to determine the position of the receivers 114, 202.

In an example, the computing device 110 can combine the motion data and the magnetic field 116 measurement(s) using a Kalman filter. For example, the motion data and the magnetic field measurements data can be fused by a Kalman filter. For example, the noisy signals from each of the IMU and the magnetic receiver(s) can be fused by the Kalman filter to improve the estimate of the position of the tracked device 104. However, other such methods of position estimation can be performed using the data received by the IMU 112 and the magnetic receiver(s) 114, 202.

Figure 3:
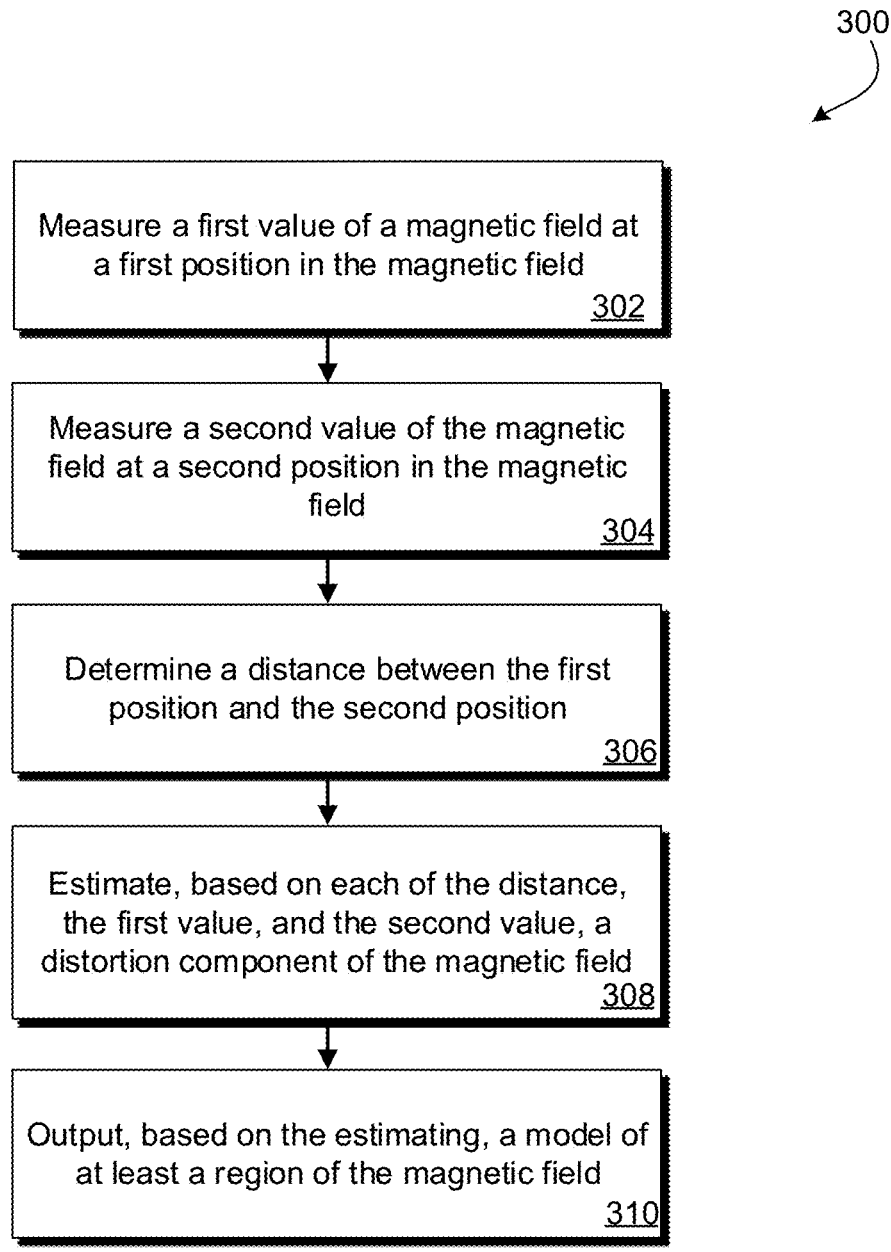
FIG. 3 shows a flow diagram representing an example process for determining distortions in a magnetic field for tracking a device in the magnetic field.

FIG. 3 shows a flow diagram representing an example process 300 for determining distortions in a magnetic field for tracking a device in the magnetic field. In process 300, the magnetic tracking system (e.g., magnetic tracking system 100 or 200 of FIGS. 1 and 2) is configured to correct the distortion for a magnetic field. The magnetic tracking system is configured to measure (302) a first value of a magnetic field at a first position in the magnetic field. As described in relation to FIGS. 1-2, a receiver 114 can record this measurement and transmit data representing the measurement to the computing device. The magnetic tracking system is configured to measure (304) a second value of the magnetic field at a second position in the magnetic field. As described in relation to FIG. 1A, the tracked device (e.g., tracked device 104) is generally moved to a different location and the receiver 114 obtains another measurement of the magnetic field 116 at the different location. As described above in relation to FIG. 2, a second receiver 202 can obtain a measurement of the magnetic field at a different position according to a distance that is known.

The magnetic tracking system is configured to determine (306) a distance between the first position and the second position. For tracked device 104, the distance is determined by measuring the trajectory by the IMU 112. For tracked device 204, the distance is known based on R2.

The magnetic tracking system is configured to estimate (308), based on each of the distance, the first value, and the second value, a distortion component of the magnetic field. The distortion values are estimated based on a generated error field map as described in relation to FIG. 1A.

The magnetic tracking system is configured to output, based on the estimating, a model of at least a region of the magnetic field. The model can include the error field map, a model of the magnetic field itself, or a portion of one or both. In some implementations, the model is used by the computing device 110 to correct a position value of the tracked device, and the corrected position is actually output to a user interface for various applications. For example, the output can include a graphical representation of the tracked device in an environment or scene corresponding to the actual, real-world environment or scene in which the magnetic tracking system is located. For example, the output can include a textual report of coordinates of the tracked device. Other such outputs are possible. The graphical representation can be output on a display, such as a head-mounted display (HMD), a surgical terminal, etc.

Figure 4:
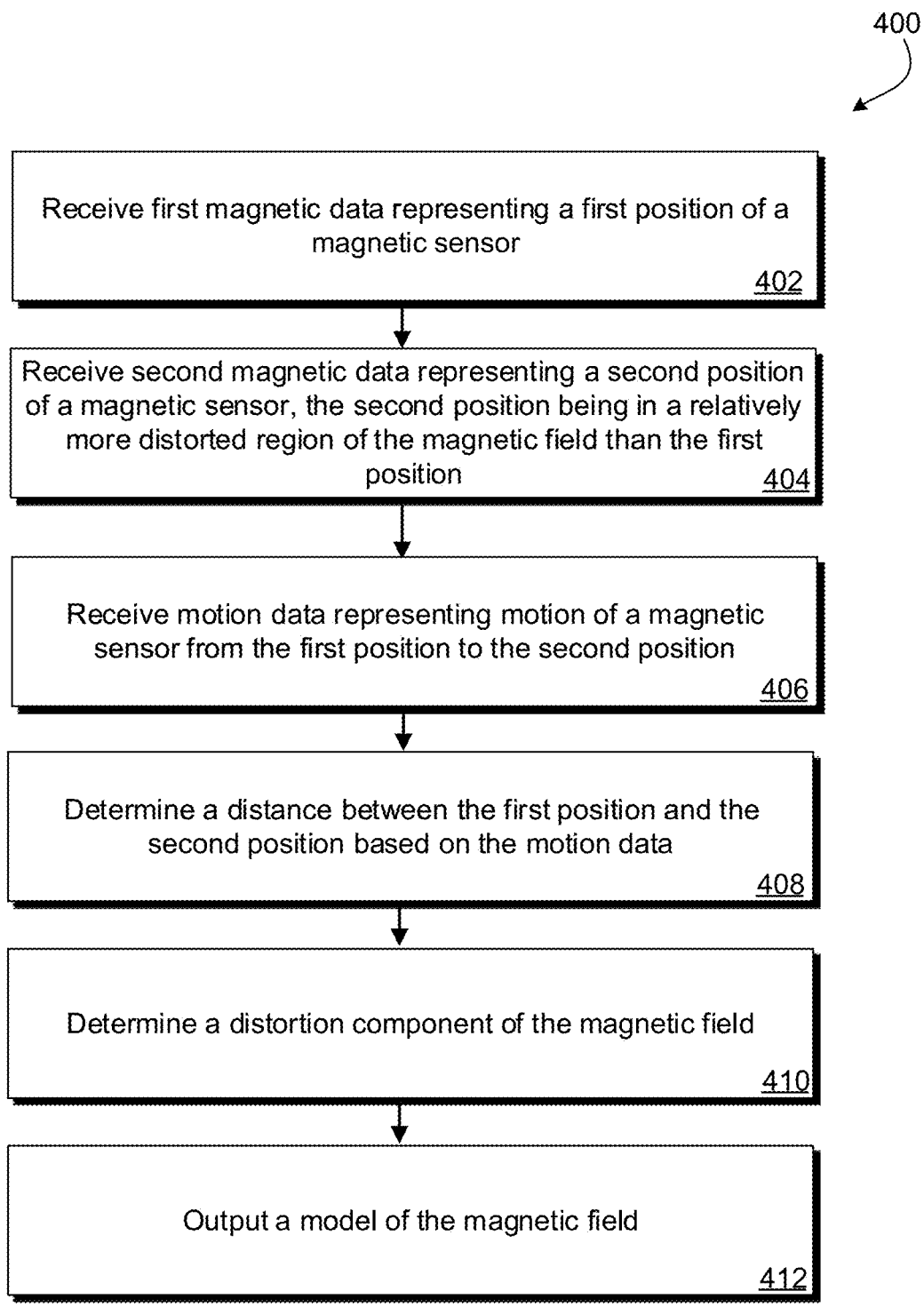
FIG. 4 shows a flow diagram representing an example process for determining distortions in a magnetic field using the magnetic tracking system of FIG. 1A.

FIG. 4 shows a flow diagram representing an example process 400 for determining distortions in a magnetic field using the magnetic tracking system of FIG. 1A. The magnetic tracking system 100 is configured to receive (402) first magnetic data representing a first position of a magnetic sensor. The magnetic tracking system 100 is configured to receive (402) second magnetic data representing a second position of a magnetic sensor, the second position being in a relatively more distorted region of the magnetic field than the first position. The magnetic tracking system 100 is configured to receive (406) motion data representing motion of a magnetic sensor from the first position to the second position. The magnetic tracking system 100 is configured to determine (408) a distance between the first position and the second position based on the motion data. The magnetic tracking system 100 is configured to determine (410) a distortion component of the magnetic field. The magnetic tracking system 100 is configured to output (412) a model of the magnetic field. Process 400 can be combined with process 300 and with variations of the processes described in relation to FIGS. 1 and 2.

Figure 5:
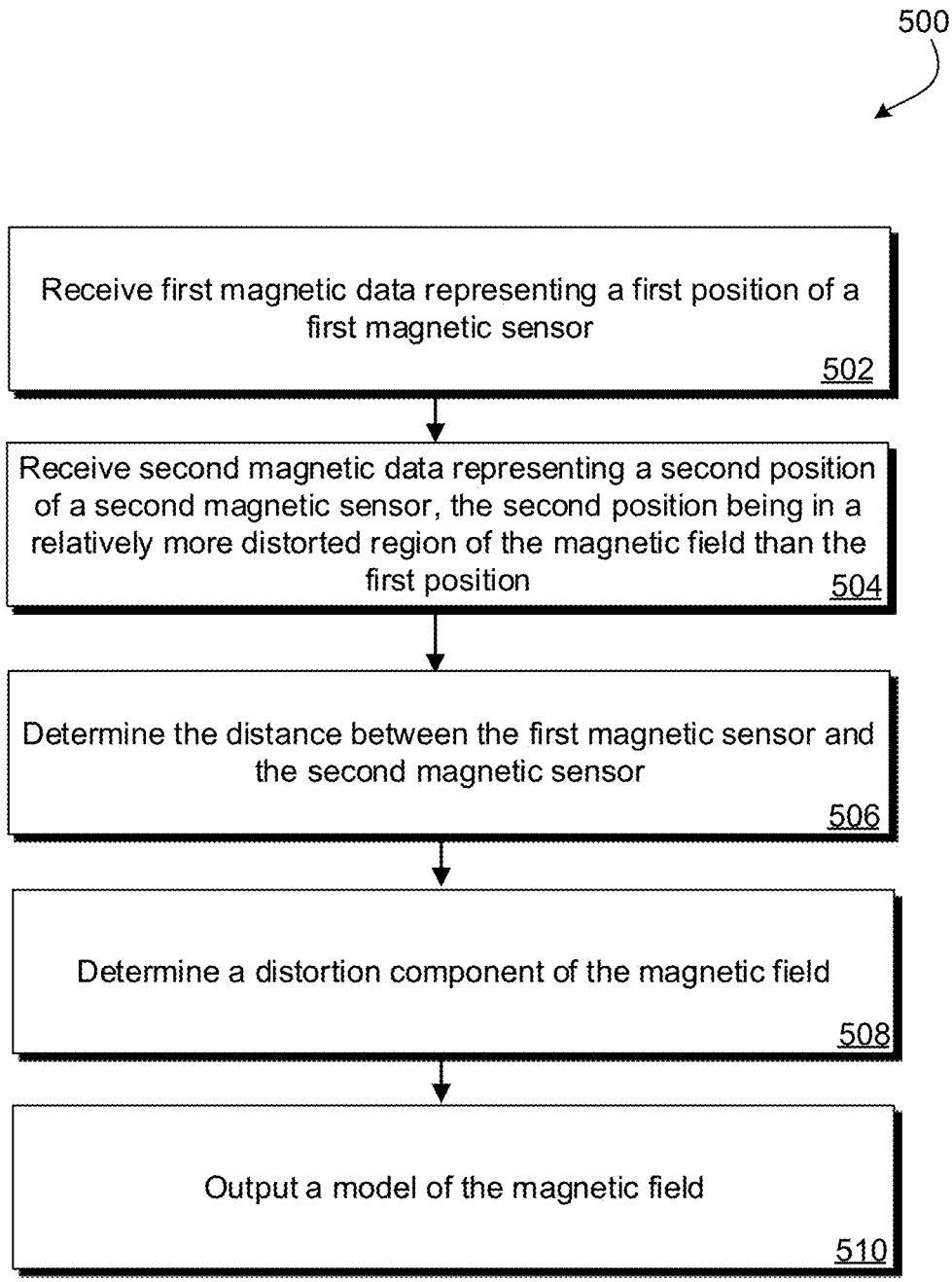
FIG. 5 shows a flow diagram representing an example process for determining distortions in a magnetic field using the magnetic tracking system of FIG. 2.

FIG. 5 shows a flow diagram representing an example process 500 for determining distortions in a magnetic field using the magnetic tracking system of FIG. 2. The magnetic tracking system 200 is configured to receive (502) first magnetic data representing a first position of a first magnetic sensor. The magnetic tracking system 200 is configured to receive (504) second magnetic data representing a second position of a second magnetic sensor, the second position being in a relatively more distorted region of the magnetic field than the first position. The magnetic tracking system 200 is configured to determine (506) the distance between the first magnetic sensor and the second magnetic sensor. The magnetic tracking system 200 is configured to determine (508) a distortion component of the magnetic field. The magnetic tracking system 200 is configured to output (510) a model of the magnetic field. Process 500 can be combined with process 300 and/or 400 and with variations of the processes described in relation to FIGS. 1 and 2.

The magnetic tracking system 100 described can be implemented using software included on a computer-readable medium for execution on a computer (e.g., the computing device 110 of FIG. 1A). For example, the software may form procedures in one or more computer programs that execute on one or more programmed or programmable computer systems (which may be of various architectures).

Figure 6:
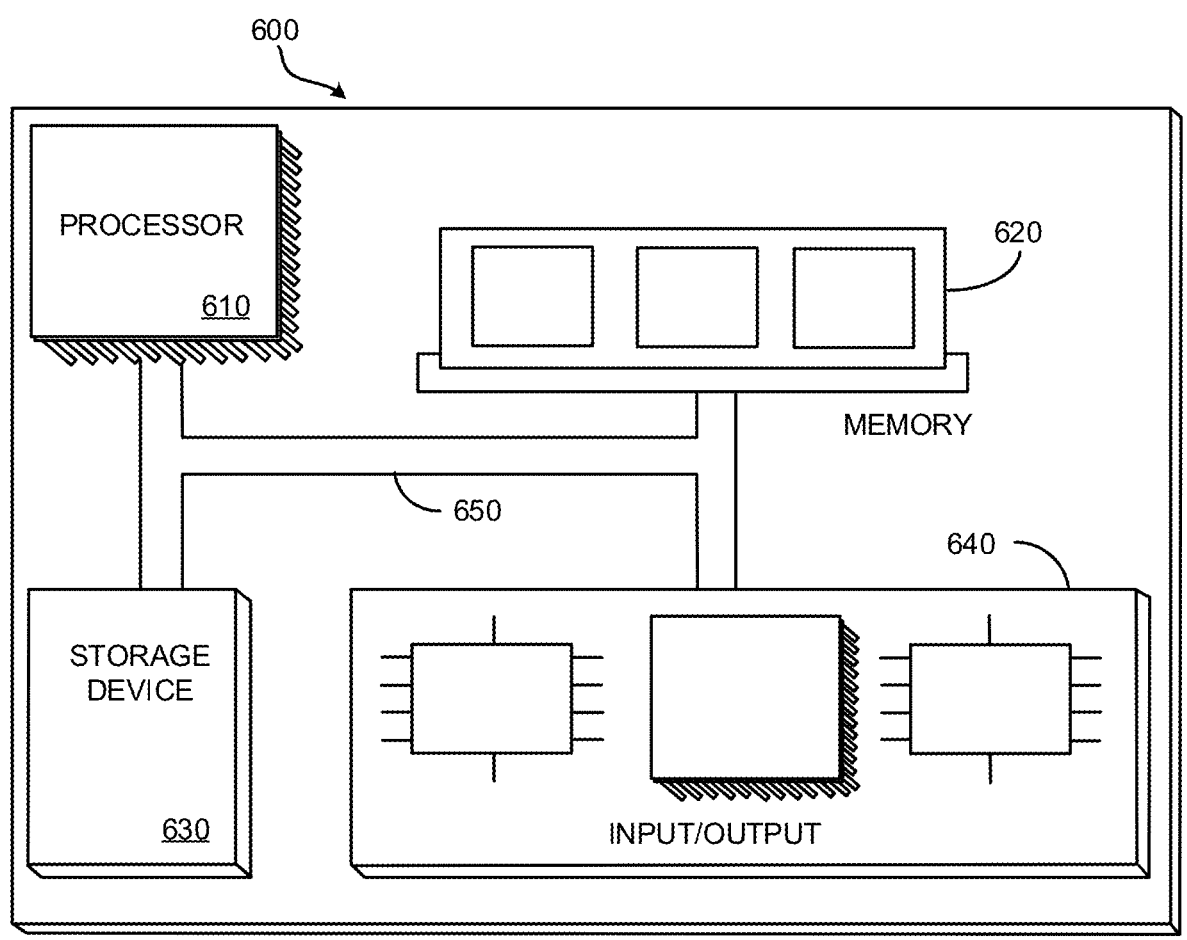
FIG. 6 is a block diagram of an example computer system.

FIG. 6 is a block diagram of an example computer system 600. The computing device 110 of FIG. 1A may be an example of the computer system 600 described here. The system 600 can include a processor 610, a memory 620, a storage device 630, and an input/output device 640. Each of the components 610, 620, 630, and 640 can be interconnected, for example, using a system bus 650. The processor 610 is capable of processing instructions for execution within the system 600. The processor 610 can be a single-threaded processor, a multi-threaded processor, or a quantum computer. The processor 610 is capable of processing instructions stored in the memory 620 or on the storage device 630. The processor 610 may execute operations such as causing the EMT system 100 to determine the position and/or the orientation of tracked device 102.

The memory 620 stores information within the system 600. In some implementations, the memory 620 is a computer-readable medium. The memory 620 can, for example, be a volatile memory unit or a non-volatile memory unit.

The storage device 630 is capable of providing mass storage for the system 600. In an aspect, the storage device 630 is a non-transitory computer-readable medium. The storage device 630 can include, for example, a hard disk device, an optical disk device, a solid-date drive, a flash drive, magnetic tape, or some other large capacity storage device. The storage device 630 may alternatively be a cloud storage device, e.g., a logical storage device including multiple physical storage devices distributed on a network and accessed using a network. In some implementations, the information stored on the memory 620 can also or instead be stored on the storage device 630.

The input/output device 640 provides input/output operations for the system 600. In some examples, the input/output device 640 includes one or more of network interface devices (e.g., an Ethernet card), a serial communication device (e.g., an RS-232 10 port), and/or a wireless interface device (e.g., a short-range wireless communication device, an 602.11 card, a 3G wireless modem, or a 4G wireless modem). Generally, the input/output device 640 includes driver devices configured to receive input data and send output data to other input/output devices, e.g., a keyboard, a printer, and display devices. In some implementations, mobile computing devices, mobile communication devices, and other devices are used.

The system 600 can include a microcontroller. A microcontroller is a device that contains multiple elements of a computer system in a single electronics package. For example, the single electronics package could contain the processor 610, the memory 620, the storage device 630, and input/output devices 640.

Although an example computer system has been described in FIG. 6, implementations of the subject matter and the functional operations described above can be implemented in other types of digital electronic circuitry, or in computer software, firmware, or hardware, including the structures disclosed in this specification and their structural equivalents, or in combinations of one or more of them. Implementations of the subject matter described in this specification can be implemented as one or more computer program products, i.e., one or more modules of computer program instructions encoded on a tangible program carrier, for example a computer-readable medium, for execution by, or to control the operation of, a processing system. The computer readable medium can be a machine readable storage device, a machine readable storage substrate, a memory device, a composition of matter effecting a machine readable propagated signal, or a combination of one or more of them.

The term "computer system" may encompass all apparatus, devices, and machines for processing data, including by way of example a programmable processor, a computer, or multiple processors or computers. A processing system can include, in addition to hardware, code that creates an execution environment for the computer program in question, e.g., code that constitutes processor firmware, a protocol stack, a database management system, an operating system, or a combination of one or more of them.

A computer program (also known as a program, software, software application, script, executable logic, or code) can be written in any form of programming language, including compiled or interpreted languages, or declarative or procedural languages, and it can be deployed in any form, including as a standalone program or as a module, component, subroutine, or other unit suitable for use in a computing environment. A computer program does not necessarily correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

Computer readable media suitable for storing computer program instructions and data include all forms of non-volatile or volatile memory, media and memory devices, including by way of example semiconductor memory devices, e.g., EPROM, EEPROM, and flash memory devices; magnetic disks, e.g., internal hard disks or removable disks or magnetic tapes; magneto optical disks; and CD-ROM and DVD-ROM disks. The processor and the memory can be supplemented by, or incorporated in, special purpose logic circuitry. The components of the system can be interconnected by any form or medium of digital data communication, e.g., a communication network. Examples of communication networks include a local area network ("LAN") and a wide area network ("WAN"), e.g., the Internet.

A number of embodiments have been described. Nevertheless, it will be understood that various modifications may be made without departing from the spirit and scope of the subject matter described herein. Other such embodiments are within the scope of the following claims.

What is claimed is:

1. A method for modeling a magnetic field, the method comprising:
    measuring, by a magnetic sensor, a first value for each of one or more characteristics of a magnetic field at a first position in the magnetic field;
    obtaining motion data representing movement of the magnetic sensor from the first position to a second position;
    measuring, by the magnetic sensor, a second value for each of the one or more characteristics of the magnetic field at the second position in the magnetic field;
    determining, by a computing device in communication with the magnetic sensor, based on the motion data, the first value for each of one or more characteristics, and the second value for each of the one or more characteristics, a distance between the first position and the second position;
    estimating a distortion component of the magnetic field at approximately the second position in the magnetic field, by the computing device in communication with the magnetic sensor based on each of the distance, the first value for each of the one or more characteristics, and the second value for each of the one or more characteristics; and
    outputting, from the computing device based on the estimating, a model of at least a region of the magnetic field.

2. The method of claim 1, wherein determining the distance between the first position and the second position in the magnetic field comprises:
    measuring, by an inertial measurement unit (IMU), the motion data representing the movement of the magnetic sensor from the first position to the second position.

3. The method of claim 1, wherein first value for each of the one or more characteristics of the magnetic field is measured by a first magnetic sensor, wherein the second value for each of the one or more characteristics of the magnetic field is measured by a second magnetic sensor that is different from the first magnetic sensor.

4. The method of claim 3, wherein the first magnetic sensor and the second magnetic sensor are connected and separated by an offset distance, and wherein the distance between the first position and the second position in the magnetic field is approximately equal to the offset distance.

5. The method of claim 1, wherein the first position is in a region of the magnetic field having less distortion than another region of the magnetic field comprising the second position.

6. The method of claim 1, wherein estimating the distortion component comprises:
retrieving a model of the magnetic field corresponding to the second position;
determining a third value of the one or more characteristics of the magnetic field corresponding to an undistorted received magnetic field at the second position according to the model; and
determining a difference between the third value for each of the one or more characteristics of the magnetic field and the second value for each of the one or more characteristics that are measured at the second position, the difference representing the distortion component of the magnetic field.

7. The method of claim 1, wherein the one or more characteristics of the magnetic field comprise a field strength of the magnetic field, the field strength based on a distance of the magnetic sensor from a transmitter configured to generate the magnetic field.

8. The method of claim 1, wherein the first value for each of one or more characteristics is measured in response to determining that the magnetic sensor is in a region of the magnetic field having approximately no distortion or that the magnetic sensor is in the region of the magnetic field having a known distortion.

9. The method of claim 8, further comprising expanding the region having the known distortion of the magnetic field, wherein the first position comprises a position in the magnetic field that is inside the region having the known distortion of the magnetic field, and wherein the second position comprises a position in the magnetic field that is outside the region having the known distortion of the magnetic field.

10. The method of claim 1, further comprising:
determining a corrected position of the magnetic sensor in the magnetic field based on the model of at least the region of the magnetic field;
generating a graphical representation of the corrected position of the magnetic sensor in the magnetic field; and
causing display of the graphical representation in a user interface.

11. A magnetic tracking system comprising:
a source device configured to generate a magnetic field;
a tracked device comprising:
a magnetic sensor configured to measure the magnetic field and generate magnetic data representing the magnetic field; and
an inertial measurement unit (IMU) configured to generate motion data based on a motion of the IMU, the IMU being coupled to the magnetic sensor; and
a computing device comprising at least one processor, the computing device configured to perform operations comprising:
receiving, from the magnetic sensor, first magnetic data representing a first position of the magnetic sensor;
receiving, from the magnetic sensor, second magnetic data representing a second position of the magnetic sensor, the second position being in a relatively more distorted region of the magnetic field than the first position;
determining a distance between the first position and the second position based on motion data received from the IMU representing motion of the magnetic sensor from the first position to the second position;
determining, based on the distance, the first magnetic data, and the second magnetic data, a distortion component of the magnetic field; and
outputting a model of the magnetic field based on the distortion component.

12. The magnetic tracking system of claim 11, further comprising:
a transmitter is configured to generate the magnetic field, wherein the transmitter is configured to generate a magnetic field comprising a plurality of axes using a plurality of transmitter axes, and wherein the magnetic sensor is configured to measure the magnetic field by measuring each of the transmitted axes of the magnetic field.

13. The magnetic tracking system of claim 11, wherein the motion data comprises linear acceleration data and angular acceleration data, and wherein the IMU comprises one or more accelerometers and one or more gyroscopes.

14. The magnetic tracking system of claim 11, wherein estimating the distortion component comprises:
retrieving a model of the magnetic field corresponding to the second position;
determining a value of the magnetic field corresponding to an undistorted received magnetic field at the second position according to the model; and
determining a difference between the value of the magnetic field and a value of the second magnetic data that is measured at the second position, the difference representing the distortion component of the magnetic field.

15. The magnetic tracking system of claim 14, the operations further comprising:
determining a corrected position of the magnetic sensor in the magnetic field based on the model the magnetic field;
generating a graphical representation of the corrected position of the magnetic sensor in the magnetic field; and
causing display of the graphical representation in a user interface.

16. A magnetic tracking system comprising:
a source device configured to generate a magnetic field;
a tracked device comprising:
a first magnetic sensor configured to measure the magnetic field and generate magnetic data representing the magnetic field at a first position relative to the source device; and
a second magnetic sensor coupled to the first magnetic sensor at a particular distance and configured to measure the magnetic field and generate magnetic data representing the magnetic field at a second position relative to the source device and at the particular distance from the first position; and
a computing device comprising at least one processor, the computing device configured to perform operations comprising:
receiving, from the first magnetic sensor, first magnetic data representing the magnetic field at the first position;

receiving, from the second magnetic sensor, second magnetic data representing the magnetic field at a second position, the second position being in a relatively more distorted region of the magnetic field than the first position;

determining, based on the particular distance, the first magnetic data, the second magnetic data, a distortion component the magnetic field by:

retrieving a model of the magnetic field corresponding to the second position;

determining a value of the magnetic field corresponding to an undistorted received magnetic field at the second position according to the model; and determining a difference between the value of the magnetic field and a value of the second magnetic data that is measured at the second position, the difference representing the distortion component of the magnetic field; and outputting a model of the magnetic field based on the distortion component.

17. The magnetic tracking system of claim 16, the operations further comprising:

determining a corrected position of the second magnetic sensor in the magnetic field based on the model the magnetic field;

generating a graphical representation of the corrected position of the second magnetic sensor in the magnetic field; and causing display of the graphical representation in a user interface.

* * * * *